US012274897B2

(12) United States Patent
Gilad

(10) Patent No.: US 12,274,897 B2
(45) Date of Patent: *Apr. 15, 2025

(54) METHOD FOR TREATING SECONDARY PULMONARY HYPERTENSION

(71) Applicant: SONIVIE LTD., Rosh Haayin (IL)

(72) Inventor: Rotem Gilad, Tel Aviv (IL)

(73) Assignee: SONIVIE LTD., Rosh Haayin (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/990,705

(22) Filed: Nov. 20, 2022

(65) Prior Publication Data

US 2023/0096801 A1 Mar. 30, 2023

Related U.S. Application Data

(63) Continuation of application No. 16/699,554, filed on Nov. 30, 2019, now Pat. No. 11,534,631, which is a
(Continued)

(51) Int. Cl.
*A61N 7/00* (2006.01)
*A61B 5/00* (2006.01)
(Continued)

(52) U.S. Cl.
CPC .......... *A61N 7/022* (2013.01); *A61B 5/02007* (2013.01); *A61B 5/021* (2013.01);
(Continued)

(58) Field of Classification Search
CPC ......... A61B 18/12; A61B 18/18; A61B 18/20; A61B 2018/00434; A61B 2018/00541;
(Continued)

(56) References Cited

U.S. PATENT DOCUMENTS 6,740,648 B2 * 5/2004 Ghazzi ................ A61P 7/10
514/217
6,970,742 B2 * 11/2005 Mann ................... A61B 5/0215
607/9
(Continued)

FOREIGN PATENT DOCUMENTS

WO 2015193889 A1 12/2015
WO 2016084081 A2 6/2016

OTHER PUBLICATIONS

Kalogeropoulos et al, "Pulmonary Hypertension and Right Ventricular Function in Advanced Heart Failure", pp. 189-198 (Year: 2011).*
(Continued)

*Primary Examiner* — Michael F Peffley
(74) *Attorney, Agent, or Firm* — The Roy Gross Law Firm, LLC; Roy D. Gross

(57) ABSTRACT

Method for ameliorating secondary pulmonary hypertension in a patient including determining a pulmonary vascular resistance (PVR) of the patient suffering from secondary pulmonary hypertension; assessing a change in the PVR in response to a selection treatment; and treating the patient with a pulmonary artery manipulation device to provide pulmonary artery denervation if the patient is determined to suffer from fixed PH, thereby ameliorating the secondary pulmonary hypertension of the patient.

11 Claims, 4 Drawing Sheets

Related U.S. Application Data continuation of application No. 15/319,790, filed as application No. PCT/IL2015/050607 on Jun. 16, 2015, now Pat. No. 10,518,112.

(60) Provisional application No. 62/013,577, filed on Jun. 18, 2014.

(51) Int. Cl.
| | |
|---|---|
| *A61B 5/02* | (2006.01) |
| *A61B 5/021* | (2006.01) |
| *A61B 5/08* | (2006.01) |
| *A61N 7/02* | (2006.01) |
| *A61B 18/00* | (2006.01) |
| *A61B 18/12* | (2006.01) |
| *A61B 18/18* | (2006.01) |
| *A61B 18/20* | (2006.01) |

(52) U.S. Cl.
CPC .............. *A61B 5/08* (2013.01); *A61B 5/4836* (2013.01); *A61B 2018/00434* (2013.01); *A61B 2018/00541* (2013.01); *A61B 18/12* (2013.01); *A61B 18/18* (2013.01); *A61B 18/20* (2013.01); *A61N 2007/003* (2013.01); *A61N 2007/0043* (2013.01)

(58) Field of Classification Search
CPC ....... A61B 5/02007; A61B 5/021; A61B 5/08; A61B 5/4836; A61N 2007/003; A61N 2007/0043; A61N 7/022
See application file for complete search history.

(56) References Cited

U.S. PATENT DOCUMENTS

| | | | | |
|---|---|---|---|---|
| 8,377,933 | B2* | 2/2013 | Gerber | A61K 31/4985 514/250 |
| 8,715,209 | B2 | 4/2014 | Gertner | |
| 9,918,776 | B2 | 3/2018 | Chen | |
| 2011/0118725 | A1* | 5/2011 | Mayse | A61B 17/00234 601/2 |
| 2011/0257562 | A1* | 10/2011 | Schaer | A61N 7/022 601/2 |
| 2013/0204068 | A1* | 8/2013 | Gnanashanmugam | A61B 18/18 601/3 |
| 2014/0180277 | A1 | 6/2014 | Chen | |
| 2015/0196357 | A1 | 7/2015 | Chen | |
| 2015/0196705 | A1 | 7/2015 | Brenneman et al. | |
| 2016/0256216 | A1 | 9/2016 | Chang et al. | |
| 2017/0128751 | A1 | 5/2017 | Gilad | |
| 2020/0238107 | A1 | 7/2020 | Shabtay et al. | |

OTHER PUBLICATIONS

Zhang et al (2016) Pulmonary artery denervation for treatment of a patient with pulmonary hypertension secondary to left heart disease, Pulmonary Circulation, 6(2):240-243, DOI: 10.1086/685550.
Natale et al (2009) Ventricular Tachycardia/fibrillation Ablation: the State of the Art Based on the VeniceChart International Consensus Document, John Wiley & Sons, p. 264, fig. 14.3.
Zhang et al (2014) Perioperative Management of Cardiovascular Diseases, published by People's Medical Publishing House, ISBN No. 7-117-18454-0.
Yin Lixue (2007) Modern Ultrasonic Cardiac Electrophysiology, published by People's Military Medical Press, ISBN No. 7-5091-1206-0.
Li Bao (2013) A Course of Cardiovascular Intervention Training, published by People's Military Medical Press, ISBN No. 978-7-5091-6440-2.
Li Yigang (2010) Clinical Key Techniques of Interventional Diagnosis and Treatment of Tachycardia, published by Science and Technology Literature Publishing, ISBN No. 978-7-5023-6528-8.
Chen et al (2013) Pulmonary Artery Denervation to Treat Pulmonary Arterial Hypertension, Journal of the American College of Cardiology, vol. 62, No. 12, pp. 1092. http:/dx.doi.org/10.1016/j.jacc.2013.05.075.
Chen et al (2013) Percutaneous pulmonary artery denervation completely abolishes experimental pulmonary arterial hypertension in vivo, EuroIntervention 9(2): 269-276, DOI: 10.4244/eijv912a43 PMID: 23466961.
Kalogeropoulos et al (2011) Pulmonary hypertension and right ventricular function in advanced heart failure, Congestive Heart Failure, 17(4):189-198, doi: 10.1111/j.1751-7133.2011.00234.x.
PCT International Search Report for International Application No. PCT/IL2015/050607, mailed Oct. 11, 2015, 5pp.
PCT Written Opinion for International Application No. PCT/IL2015/050607, mailed Oct. 11, 2015, 7pp.
PCT International Preliminary Report on Patentability for International Application No. PCT/IL2015/050607, issued Dec. 20, 2016, 8pp.
Leopold (2015). Catheter-based therapies for patients with medication-refractory pulmonary arterial hypertension. Circulation: Cardiovascular Interventions, 8(11), e003332.
Oral et al (2006) Circumferential pulmonary-vein ablation for chronic atrial fibrillation. New England Journal of Medicine, 354(9), 934-941.
Heart failure with preserved Ejection Fraction (H FpEF). Heart Failure with Preserved Ejection Fraction (H FpEF) I Frankel Cardiovascular Center I Michigan Medicine. (Mar. 13, 2017). https://www.umcvc.org/conditions-treatments/heart-fai lure-preserved-ejection-fraction-hfpef (Year: 2017).
Khan, M. N., Jaïs, P., Cummings, J., Di Biase, L., Sanders, P., Martin, D. O., ... & Natale, A. (2008). Pulmonary-vein isolation for atrial fibrillation in patients with heart failure. New England Journal of Medicine, 359(17), 1778-1785. doi: 10.1056/NEJMoa0708234. PMID: 18946063.
Anter, E., Jessup, M., & Callans, D. J. (2009). Atrial fibrillation and heart failure: treatment considerations for a dual epidemic. Circulation, 119(18), 2516-2525. doi: 10.1161/CIRCULATIONAHA.108.821306. PMID: 19433768.
Sinelnikov, Y. D., Fjield, T., & Sapozhnikov, O. A. (2009). The mechanism of lesion formation by focused ultrasound ablation catheter for treatment of atrial fibrillation. Acoustical physics, 55, 647-656. doi: 10.1134/S1063771009040216. PMID: 20161431; PMCID: PMC2786241.
Ad, N., Henry, L., & Hunt, S. (2011). The impact of surgical ablation in patients with low ejection fraction, heart failure, and atrial fibrillation. European journal of cardio-thoracic surgery, 40(1), 70-76. doi: 10.1016/j.ejcts.2010.11.016. Epub Dec. 18, 2010. PMID: 21169029.
Hynynen, K., Dennie, J., Zimmer, J. E., Simmons, W. N., He, D. S., Marcus, F. I., & Aguirre, M. (1997). Cylindrical ultrasonic transducers for cardiac catheter ablation. IEEE Transactions on biomedical engineering, 44(2), 144-151. doi: 10.1109/10.552244. PMID: 9214794.
Becker, R., & Schoels, W. (2004). Ablation of atrial fibrillation: Energy sources and navigation tools: A review. Journal of Electrocardiology, 37 Suppl:55-62. doi: 10.1016/j.jelectrocard.2004.08.016. PMID: 15534801.
Hsu, L. F., Jaïs, P., Sanders, P., Garrigue, S., Hocini, M., Sacher, F., ... & Haïssaguerre, M. (2004). Catheter ablation for atrial fibrillation in congestive heart failure. New England Journal of Medicine, 351(23), 2373-2383. DOI: 10.1056/ NEJMoa041018.
Pappone, C., Augello, G., Sala, S., Gugliotta, F., Vicedomini, G., Gulletta, S., ... & Santinelli, V. (2006). A randomized trial of circumferential pulmonary vein ablation versus antiarrhythmic drug therapy in paroxysmal atrial fibrillation: the APAF Study. Journal of the American College of Cardiology, 48(11), 2340-2347. doi: 10.1016/j.jacc.2006.08.037. Epub Oct. 16, 2006. PMID: 17161267.

(56) References Cited

OTHER PUBLICATIONS

Greillier, P., Bawiec, C., Bessière, F., & Lafon, C. (2018). Therapeutic Ultrasound for the Heart: state of the Art. IRBM, 39(4), 227-235. https://doi.org/10.1016/j.irbm.2017.11.004.

* cited by examiner

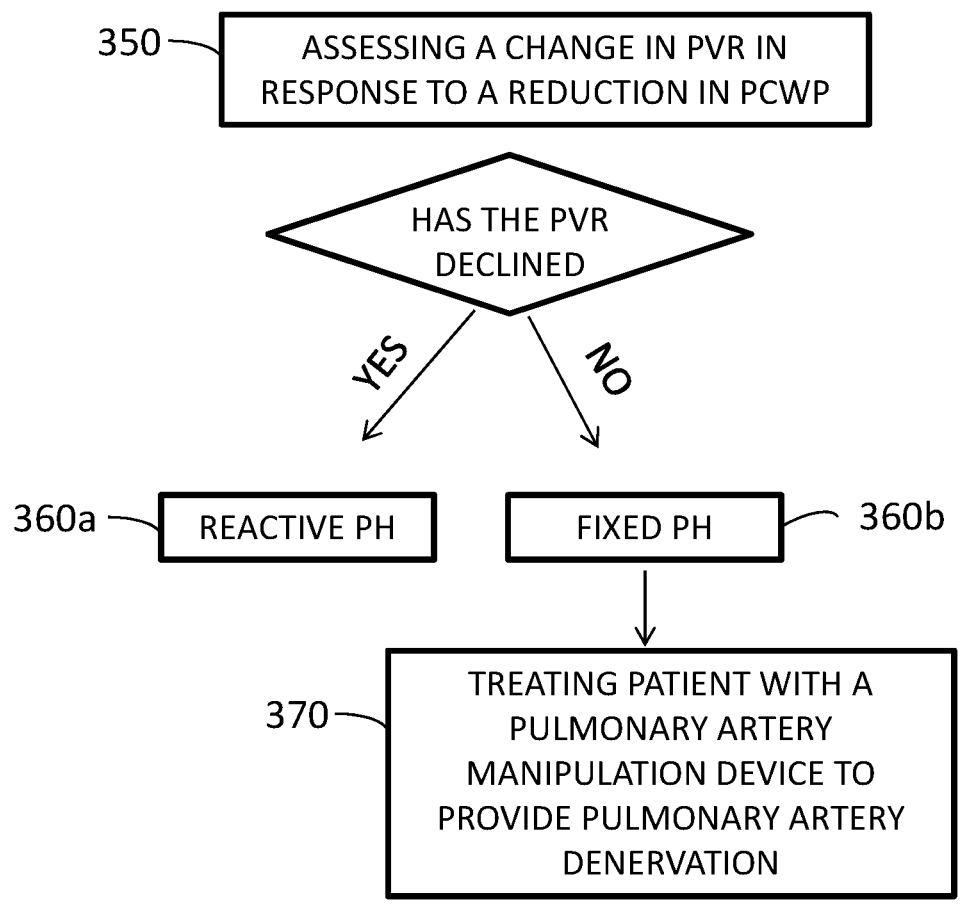
FIGURE 3 - CONTINUED

METHOD FOR TREATING SECONDARY PULMONARY HYPERTENSION

CROSS REFERENCE TO RELATED APPLICATIONS

This application is a continuation of U.S. Ser. No. 16/699,554 filed on Nov. 30, 2019, (issued as U.S. Pat. No. 11,534,631) which is a continuation of U.S. Ser. No. 15/319,790 filed Dec. 18, 2019 (issued as U.S. Pat. No. 10,518,112), which is a 35 U.S.C. § 371 national phase application of PCT/IL2015/050607, filed Jun. 16, 2015, which claims priority to U.S. 62/013,577 filed on Jun. 18, 2014. All applications are incorporated herein by reference as if fully set forth in their entirety.

TECHNICAL FIELD

The present disclosure relates generally to the field of pulmonary artery denervation in the treatment of secondary pulmonary hypertension.

BACKGROUND

Pulmonary hypertension (PH) is an increase in blood pressure in the pulmonary artery, pulmonary vein, or pulmonary capillaries, together known as the lung vasculature.

It is a disease phenomenon of multifactorial etiology with high mortality. The disease causes increased work for the right side of the heart and eventually hypertrophy and dysfunction, often in both the right and left side of the heart. Despite improvements in therapy, the prognosis of pulmonary hypertension is poor, with median survival being around 5 years.

Typically, patients suffering from PH are treated with pharmacological agents which are extremely expensive (as much as $100,000 per year for an adult) and still not entirely-efficacious. Moreover, treatment outcome amongst patients suffering from PH is highly variable, mainly due to the variance in underlying factors.

A distinction has been made between primary and secondary PH.

Primary PH (WHO group I PH—Pulmonary arterial hypertension (PAH)) involves the vasoconstriction or tightening of blood vessels connected to and within the lungs. This makes it harder for the heart to pump blood through the lungs. Over time, the increased workload of the heart causes hypertrophy of the right ventricle, making the heart less able to pump blood through the lungs, ultimately causing right heart failure.

Secondary PH can again be divided into four forms of PH, each having a distinct underlying etiology.

WHO Group II PH refers to a secondary PH in which the PH is owing to left heart disease. The pathogenesis in WHO Group II PH is entirely different from that of WHO Group I in that constriction or damage to the pulmonary blood vessels is not the issue. Instead, the left heart fails to pump blood efficiently, leading to pooling of blood in the lungs and back pressure within the pulmonary system. This causes pulmonary edema and pleural effusions.

WHO Group III PH refers to a secondary PH in which the PH is owing to hypoxia. The low levels of oxygen are thought to cause vasoconstriction or tightening of pulmonary arteries, hypoxic pulmonary vasoconstriction. When prolonged, the hypoxia-mediated vasoconstriction occurs across a large portion of the pulmonary vascular bed and eventually brings about pulmonary hypertension. Non-limiting examples of WHO group III PH include chronic obstructive pulmonary disease (COPD) associated PH and interstitial lung disease (ILD) associated PH.

WHO Group IV refers to a secondary PH in which the PH is owing to chronic thromboembolic pulmonary hypertension. In this case, the blood vessels are blocked or narrowed with recurrent blood clots, which often cause the blood vessels to constrict. This combination of blocked or narrowed vessels and vasoconstriction once again increases the resistance to blood flow and so the pressure within the system rises.

WHO Group IV refers to a secondary PH in which the underlying cause of the PH is unknown.

SUMMARY

Aspects of the disclosure, in some embodiments thereof, relate to a method for ameliorating secondary pulmonary hypertension (PH) by pulmonary artery denervation. In aspects thereof, the method relates to positioning a pulmonary artery manipulation device in or in proximity to a target blood vessel, within the pulmonary vasculature of a patient suffering from secondary pulmonary hypertension and impairing the activity of at least one sympathetic nerve, nerve fiber or neuron, using the pulmonary artery manipulation device. The impairment of the nerve, nerve fiber or neuron leads to denervation of the target blood vessel and as a result thereof to amelioration of the secondary PH.

In other aspects thereof, the method relates to selecting patients who are likely to be susceptible to the denervation treatment prior to the treatment. According to some embodiments, the susceptibility of the patient is evaluated by determining a pulmonary vascular resistance (PVR) of the patient and assessing a change in the PVR in response to a selection treatment.

Advantageously, the method disclosed herein may take into account the underlying cause of the PH. Most treatments available today are directed to only a small subset of patients, namely patients suffering from idiopathic pulmonary arterial hypertension (IPAH—WHO Group I PH), who are typically treated with phosphodiesterase type 5 (PDE5) inhibitors, endothelin receptor antagonists and prostacyclins.

However, many patients suffering from PH, in particular patients suffering from WHO group II and III PH, are resistant to most conventional PH treatments. The method disclosed herein advantageously provides a treatment of patients suffering from secondary PH who often have no real treatment option available. According to some embodiments, the method is capable of identifying patients suffering from secondary PH, who are likely to benefit from pulmonary artery denervation treatment. Thus, the method, on the one hand, provides an efficient treatment solution to patients for whom no efficient treatment is currently available and, on the other hand, avoids treating patients who are unlikely to benefit from the treatment, thereby reducing unnecessary pain, side effects, inconvenience and expenses.

According to some embodiments, there is provided a method for ameliorating secondary pulmonary hypertension. According to some embodiments, the method includes positioning a pulmonary artery manipulation device in a target blood vessel, within the pulmonary vasculature of a patient suffering from secondary pulmonary hypertension and impairing the activity of at least one sympathetic nerve, nerve fiber or neuron, using the pulmonary artery manipulation device, to denervate the target blood vessel, thereby ameliorating the secondary pulmonary hypertension of the patient.

According to some embodiments, the secondary pulmonary hypertension may include WHO group II pulmonary hypertension, WHO group III pulmonary hypertension, WHO group IV pulmonary hypertension, or WHO group V pulmonary hypertension. According to some embodiments, WHO group II pulmonary hypertension may include left heart disease associated pulmonary hypertension. According to some embodiments, WHO group III pulmonary hypertension may include, but is not limited to, chronic obstructive pulmonary disease associated pulmonary hypertension and/or interstitial lung disease associated pulmonary hypertension. According to some embodiments, WHO group IV pulmonary hypertension may include chronic thromboembolic associated pulmonary hypertension. According to some embodiments, WHO group V pulmonary hypertension may include connective tissue disease associated pulmonary hypertension.

According to some embodiments, ameliorating secondary pulmonary hypertension of the patient may include decreasing the pulmonary vascular resistance (PVR) in at least one artery of the pulmonary vasculature. According to some embodiments, the PVR of the patient is at least 2.5 Wood units. According to some embodiments, the PVR of the patient remains essentially unchanged when a pulmonary capillary wedge pressure (PCWP) of the patient is reduced. According to some embodiments, the PVR of the patient remains essentially unchanged when the patient is treated with a diuretic and/or a vasodilator.

According to some embodiments, patients suffering from secondary pulmonary hypertension may include patients with a pre-capillary and post capillary involvement.

According to some embodiments, innervating the target blood vessel may include reducing a tone of smooth muscles within a wall of the target blood vessel.

According to some embodiments, impairing the activity of at least one sympathetic nerve, nerve fiber or neuron may include emitting an ultrasound beam from the pulmonary artery manipulation device. According to some embodiments, the ultrasound beam may be an unfocused ultrasound beam. According to some embodiments, the ultrasound beam may be emitted at a frequency of 1-50 Mhz. According to some embodiments, the ultrasound beam may be emitted at a frequency of 10-40 Mhz.

According to some embodiments, there is provided a method for ameliorating secondary pulmonary hypertension in a patient. According to some embodiments, the method may include determining a pulmonary vascular resistance (PVR) of the patient; assessing a change in the PVR in response to a selection treatment; and treating the patient with a pulmonary artery manipulation device to provide pulmonary artery denervation if the determined PVR is above 2.5 Wood units and if essentially no change in the PVR is obtained in response to the selection treatment, thereby ameliorating the secondary pulmonary hypertension of the patient.

According to some embodiments, the secondary pulmonary hypertension may include WHO group II pulmonary hypertension and/or WHO group III pulmonary hypertension. According to some embodiments, WHO group II pulmonary hypertension may include left heart disease associated pulmonary hypertension. According to some embodiments, WHO group III pulmonary hypertension may include chronic obstructive pulmonary disease pulmonary hypertension and/or interstitial lung disease associated pulmonary hypertension.

According to some embodiments, the method further includes determining a pulmonary capillary wedge pressure (PCWP) and/or a left ventricular end-diastolic pressure (LVEDP). According to some embodiments, when the PCWP is above 15 mmHg and the LVEDP is above 18 mmHg, the secondary pulmonary hypertension is WHO group II pulmonary hypertension.

According to some embodiments, the selection treatment may include treating the patient with diuretics, vasodilators, chronic heart failure treatments, antihypertensives, or any combination thereof. According to some embodiments, the vasodilator may include: calcium channel blockers, ACE inhibitors, beta blockers, digoxin, Theophylline, PDE5 inhibitors, prostacyclins, endothelin receptor antagonists or any combination thereof.

According to some embodiments, the selection treatment may further include: exercise, right heart catheterization, volume challenge during right heart catherization, cardiac echo, CT, MM, pulmonary angiogram, spirometry, lung volume assessment, or any combination thereof.

According to some embodiments, treating the patient with a pulmonary artery manipulation device may include positioning a pulmonary artery manipulation device in a pulmonary artery, and impairing the activity of at least one sympathetic nerve, nerve fiber or neuron, thereby denervating the pulmonary artery.

According to some embodiments, the pulmonary artery manipulation device may be configured to emit an ultrasound beam. According to some embodiments, the ultrasound beam is an unfocused ultrasound beam. According to some embodiments, the ultrasound beam is emitted at a frequency of 1-50 Mhz. According to some embodiments, the ultrasound beam is emitted at a frequency of 10-40 Mhz.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Some embodiments of the disclosure are described herein with reference to the accompanying figures. The description, together with the figures, makes apparent to a person having ordinary skill in the art how some embodiments of the disclosure may be practiced. The figures are for the purpose of illustrative purposes only.

DETAILED DESCRIPTION

Figure 1:
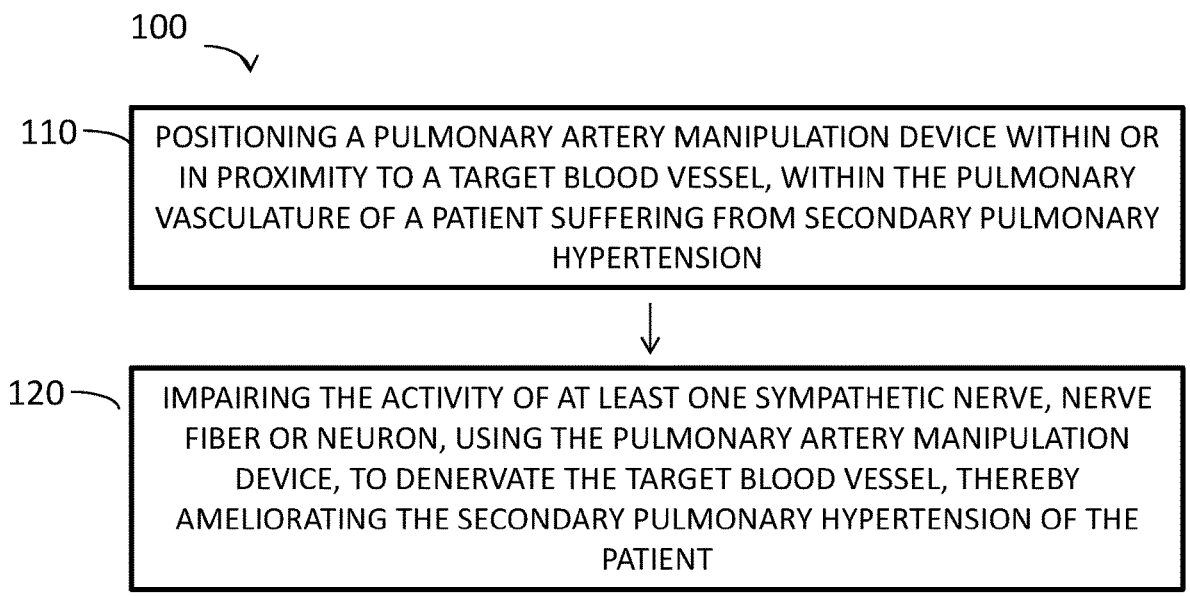
FIG. 1 is an illustrative flowchart of a method for ameliorating secondary pulmonary hypertension, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

The present disclosure relates generally to the field of pulmonary artery denervation in the treatment of secondary pulmonary hypertension.

According to some embodiments, there is provided a method for ameliorating secondary pulmonary hypertension. According to some embodiments, the method includes positioning a pulmonary artery manipulation device in proximity to a target blood vessel within the pulmonary vasculature of a patient suffering from secondary pulmonary hypertension.

As used herein the term "pulmonary artery manipulation device" may refer to any device configured to bring about vasodilation, and/or reduced pulmonary vascular resistance, and/or reduced pulmonary hypertension. According to some embodiments, the pulmonary artery manipulation device may include an intravascular treatment device. According to some embodiments, the pulmonary artery manipulation device may include a device configured to cause pulmonary artery denervation.

According to some embodiments, the pulmonary artery manipulation device may include a radiofrequency emitter. According to some embodiments, the pulmonary artery manipulation device may include a modified radiofrequency emitter. According to some embodiments, the pulmonary artery manipulation device may include a laser.

According to some embodiments, the pulmonary artery manipulation device may include a catheter and an ultrasound emitter mounted on the catheter. According to some embodiments, the ultrasound beam may be an unfocused ultrasound beam. According to some embodiments, the ultrasound beam may be a high intensity focused ultrasound beam. According to some embodiments, the ultrasound beam may be a low frequency ultrasound beam. According to some embodiments, the ultrasound beam may be emitted at a frequency of 1-100 Mhz, 1-50 Mhz, 5-50 Mhz, 10-40 Mhz or any other suitable frequency. Each possibility is a separate embodiment.

According to some embodiments the method includes positioning a pulmonary artery manipulation device within or in proximity to a target blood vessel.

As used herein the term "proximity" may refer to the pulmonary artery manipulation device touching the target blood vessel or to the pulmonary artery manipulation device being distanced 1 mm, 2 mm, 5 mm, 1 cm or more from the wall of the target blood vessel. Each possibility is a separate embodiment.

According to some embodiments, positioning a treatment device within or in proximity to a target blood vessel may impair the activity of at least one sympathetic nerve, nerve fiber or neuron. According to some embodiments, impairing the activity of at least one sympathetic nerve, nerve fiber or neuron may denervate the target blood vessel, thereby ameliorating the secondary pulmonary hypertension of the patient.

As referred to herein, the terms "patient" and "subject" may interchangeably be used and may relate to a subject suffering from secondary pulmonary hypertension and/or a patient susceptible to pulmonary artery denervation for treating secondary pulmonary hypertension.

According to some embodiments, pulmonary hypertension (PH) may be defined by a mean pulmonary artery pressure (mPAP) of above 20 mmHg, above 25 mmHg, above 30 mmHg or more. Each possibility is a separate embodiment.

As referred to herein, the term "secondary pulmonary hypertension" may refer to a PH which is not a result of pulmonary arterial hypertension.

According to some embodiments, the secondary pulmonary hypertension may include WHO group II pulmonary hypertension, WHO group III pulmonary hypertension, WHO group IV pulmonary hypertension or WHO group V pulmonary hypertension. According to some embodiments, WHO group II pulmonary hypertension may include left heart disease associated pulmonary hypertension. According to some embodiments, WHO group III pulmonary hypertension may include, but is not limited to chronic obstructive pulmonary disease associated pulmonary hypertension and/or interstitial lung disease associated pulmonary hypertension. According to some embodiments, WHO group IV pulmonary hypertension may include chronic thromboembolic associated pulmonary hypertension. According to some embodiments, WHO group V pulmonary hypertension may include connective tissue disease associated pulmonary hypertension.

According to some embodiments, a patient suffering from secondary PH may include patients with a pre-capillary pulmonary arterial contribution to the PH. According to some embodiments, a pre-capillary pulmonary arterial contribution to PH may be reflected by an increased transpulmonary gradient (TPG). As used herein, the term "transpulmonary gradient" may refer to the difference between mean pulmonary arterial pressure (mPAP) and left atrial pressure (PLA; commonly estimated by pulmonary capillary wedge pressure: PPCW). According to some embodiments, an increased TPG may refer to an mPAP-PCWP that exceeds 12-15 mmHg. According to some embodiments, a pre-capillary pulmonary arterial contribution to PH may be reflected by an elevated pulmonary vascular resistance (PVR). According to some embodiments, an elevated PVR may refer to a PVR above 2 Wood units, above 2.5 Wood units, above 3 Wood units or above 3.5 Wood units. According to some embodiments, a patient suffering from secondary PH may include patients having a mixed PH. According to some embodiments, the term "mixed PH" may refer to PH having both pre- and a post-capillary contributions to the elevated pulmonary arterial pressure.

According to some embodiments, ameliorating secondary pulmonary hypertension of the patient may include decreasing the pulmonary vascular resistance (PVR) in at least one artery of the pulmonary vasculature. According to some embodiments, the PVR of the patient is at least 2.5 Wood units. According to some embodiments, the PVR of the patient remains essentially unchanged when a pulmonary capillary wedge pressure (PCWP) of the patient is reduced. According to some embodiments, the PVR of the patient remains essentially unchanged when the patient is treated with a diuretic and/or a vasodilator.

According to some embodiments, patients suffering from secondary pulmonary hypertension may include patients with a pre-capillary and post capillary involvement.

According to some embodiments, impairing the activity of at least one sympathetic nerve, nerve fiber or neuron may refer to the process of partial or complete nerve destruction, which may be referred to herein as "denervating" or "denervation" of a structure. According to some embodiments, impairing the activity of at least one sympathetic nerve may refer to impairing the activity of at least one efferent sympathetic nerve fiber spreading from the pulmonary trunk toward the lungs. According to some embodiments, the method may involve denervating one or more arteries supplying the lungs, such as, but not limited to, the pulmonary trunk, the left pulmonary artery and/or the right pulmonary artery.

According to some embodiments, innervating the target blood vessel may include reducing a tone of smooth muscles within a wall of the target blood vessel.

According to some embodiments, impairing the activity of at least one nerve, nerve fiber or neuron may include providing monopolar radiofrequency, bipolar radiofrequency, ultrasound, light heat, cold radiation, microwave radiation, phototherapy, magnetic therapy, electro magnetical radiation, electrotherapy, cryotherapy, plasma therapy, mechanical manipulation, kinetic therapy, nuclear therapy, elastic and hydrodynamic energy.

According to some embodiments, impairing the activity of at least one nerve, nerve fiber or neuron may include emitting an ultrasound beam from the pulmonary artery manipulation device.

According to some embodiments, there is provided a method for ameliorating secondary pulmonary hypertension in a patient. According to some embodiments, the method may include determining a pulmonary vascular resistance (PVR) of the patient; assessing a change in the PVR in response to a selection treatment; and treating the patient with a pulmonary artery manipulation device to provide pulmonary artery denervation if the determined PVR is above 2.0, above 2.5, above 3.0, above 3.5 Wood units or more and if essentially no change in the PVR is obtained in response to the selection treatment, thereby ameliorating the secondary pulmonary hypertension of the patient. Each possibility is a separate embodiment.

According to some embodiments, there is provided a method for ameliorating secondary pulmonary hypertension in a patient. According to some embodiments, the method may include determining a pulmonary vascular resistance (PVR) of the patient; assessing a change in the PVR in response to a selection treatment; and providing a pulmonary artery manipulation treatment to cause pulmonary artery denervation if the determined PVR is above 2.0, above 2.5, above 3.0, above 3.5 Wood units or more and if essentially no change in the PVR is obtained in response to the selection providing a pulmonary artery manipulation treatment, thereby ameliorating the secondary pulmonary hypertension of the patient. Each possibility is a separate embodiment.

As used herein, the term "pulmonary artery manipulation treatment" may refer to any treatment configured to bring about vasodilation, and/or reduced pulmonary vascular resistance, and/or reduced pulmonary hypertension. According to some embodiments, the pulmonary artery manipulation treatment may include pulmonary artery denervation. According to some embodiments, the pulmonary artery manipulation treatment may include treating the patients with medicaments, such as, but not limited to, diuretics and/or vasodilators. According to some embodiments, chemical substances can be used and introduced intraluminally to impact neural elements. According to some embodiments, chemical substances can be used and introduced extraluminally to impact neural elements.

According to some embodiments, the secondary pulmonary hypertension may include WHO group II pulmonary hypertension, WHO group III pulmonary hypertension, WHO group IV pulmonary hypertension or WHO group V pulmonary hypertension. According to some embodiments, WHO group II pulmonary hypertension may include left heart disease associated pulmonary hypertension. According to some embodiments, WHO group III pulmonary hypertension may include chronic obstructive pulmonary disease pulmonary hypertension and/or interstitial lung disease associated pulmonary hypertension. According to some embodiments, WHO group IV pulmonary hypertension may include chronic thromboembolic associated pulmonary hypertension. According to some embodiments, WHO group V pulmonary hypertension may include connective tissue disease associated pulmonary hypertension.

According to some embodiments, PVR may refer to the resistance, offered by the vasculature of the lungs, that must be overcome to push blood through the circulatory system. According to some embodiments, determining the PVR of a patient may include computing a PVR value based on a mean pulmonary arterial pressure (mPAP), a pulmonary capillary wedge pressure (PCWP) and a cardiac output of the patient.

As used herein, the term "selection treatment" may refer to a treatment and/or challenge configured to alleviate a primary cause of PH. According to some embodiments, the selection treatment is provided a short-term treatment for selection purposes. Alternatively, the selection treatment may be part of a routine treatment of the patient.

According to some embodiments, patients susceptible to pulmonary artery denervation may include patients resistant to the treatment selection. According to some embodiments, patients susceptible to pulmonary artery denervation may include patients with a PVR above 2.0 mmHg, above 2.5 mmHg, above 3.0 mmHg or more. Each possibility is a separate embodiment. According to some embodiments, patients susceptible to pulmonary artery denervation may include patients in whom essentially no change in the PVR is obtained in response to the selection treatment, also referred to herein patients having a fixed PH. As used herein, the term "essentially" when referring to a change in the PVR may refer to a change of less than ±0.5 mmHg, less than ±0.25 mmHg or less than ±0.1 mmHg. Each possibility is a separate embodiment.

According to some embodiments, suitable selection treatments may include, but are not limited to, diuretics, vasodilators, chronic heart failure treatments, oxygen, antihypertensives, or any combination thereof. According to some embodiments, the treatment may include: calcium channel blockers, ACE inhibitors, beta blockers, digoxin, theophylline, phosphodiesterase type 5 (PDE5) inhibitors, prostacyclins, endothelin receptor antagonists, nitric oxide, adenosine or any combination thereof. Each possibility is a separate embodiment.

As a non-limiting example, in patients suffering from WHO group II PH, the selection treatment may include reducing the PCWP. According to some embodiments, reducing the PCWP may include treating the patient with diuretics and/or vasodilators, such as, but not limited to, PDE5 inhibitors.

As an additional non-limiting example, in patients suffering from WHO group III PH, the selection treatment may include treating the patient with a systemic vasodilator such as, but not limited to, theophylline or a calcium channel blocker (CCB).

According to some embodiments, the selection treatment may further include: exercise, intravascular volume challenge, right heart catheterization, volume challenge during right heart catherization, cardiac echo, CT, MRI, pulmonary angiogram, ECG, spirometry, lung volume assessment, lung ventilation/perfusion (VQ) scan, blood tests (including: arterial gasses, blood count, chemistry, liver function and hormones), or any combination thereof. Each possibility is a separate embodiment.

As a non-limiting example, the treatment selection may include assessing a relative change in mPAP and cardiac output (flow) during exercise (i.e. a higher increase in mPAP relative to flow may be indicative of the patient being susceptible to pulmonary artery denervation).

According to some embodiments, the method may further include determining a pulmonary capillary wedge pressure (PCWP) and/or a left ventricular end-diastolic pressure (LVEDP). According to some embodiments, when the PCWP is above 12 mmHg, above 13 mmHg, above 14 mmHg, above 15 mmHg or above 16 mmHg and the LVEDP is above 15 mmHg, above 16 mmHg, above 17 mmHg, above 18 mmHg or above 20 mmHg, the secondary pulmonary hypertension is WHO group II pulmonary hypertension. Each possibility is a separate embodiment.

According to some embodiments, treating the patient with a pulmonary artery manipulation device may include positioning the pulmonary artery manipulation device in a pulmonary artery, and impairing the activity of at least one sympathetic nerve, nerve fiber or neuron, thereby denervating the pulmonary artery.

Reference is now made to FIG. 1 which is an illustrative flowchart of a method 100 for ameliorating secondary pulmonary hypertension, according to some embodiments. In step 110 a pulmonary artery manipulation device is positioned in a target blood vessel, within the pulmonary vasculature of a patient suffering from secondary pulmonary hypertension. In step 120 the activity of at least one sympathetic nerve is impaired in order to denervate the target blood vessel and thereby ameliorating the secondary pulmonary hypertension of the patient.

Figure 2:
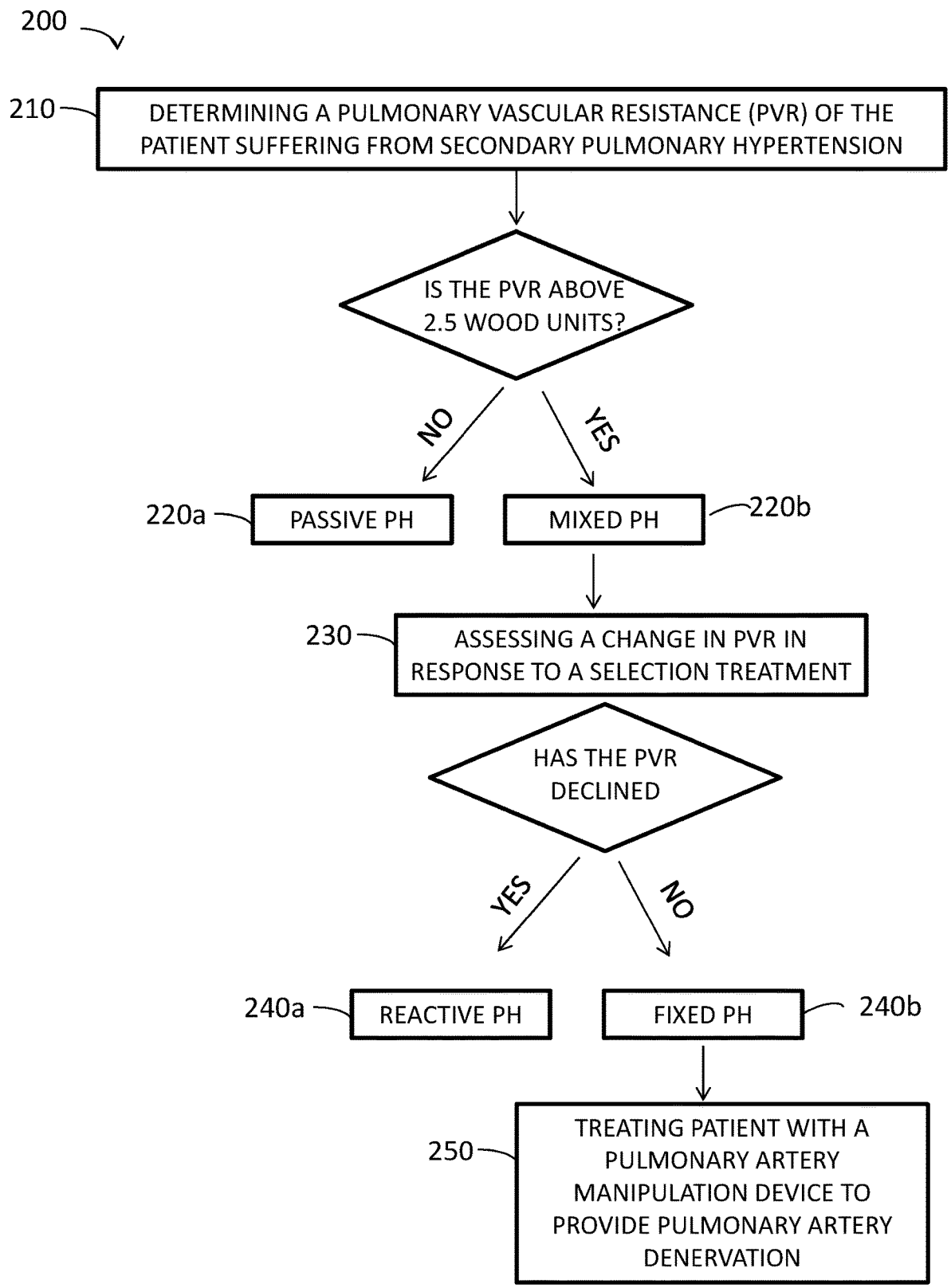
FIG. 2 is an illustrative flowchart of a method for ameliorating secondary pulmonary hypertension, according to some embodiments.

Reference is now made to FIG. 2 which is an illustrative flowchart of a method 200 for ameliorating secondary pulmonary hypertension, according to some embodiments. In step 210 a pulmonary vascular resistance (PVR) of a patient suffering from secondary pulmonary hypertension is determined. If the PVR is not above 2.5 Wood units (or another suitable predetermined value, as described herein), passive PH is determined, as in step 220a and no further action is taken. If the PVR is above 2.5 Wood units, mixed PH is determined, as in step 220b and the method proceeds to step 230. In step 230 a change in the PVR in response to a selection treatment is determined. If the PVR has declined, the PH is determined to be reactive, as in step 240a and no further action is taken. If the PVR has not declined, the PH is determined to be fixed (i.e. non-reactive) as in step 240b, and the method proceeds to step 250. In step 250 the patient is treated with a pulmonary artery manipulation device to provide pulmonary artery denervation.

Figure 3:
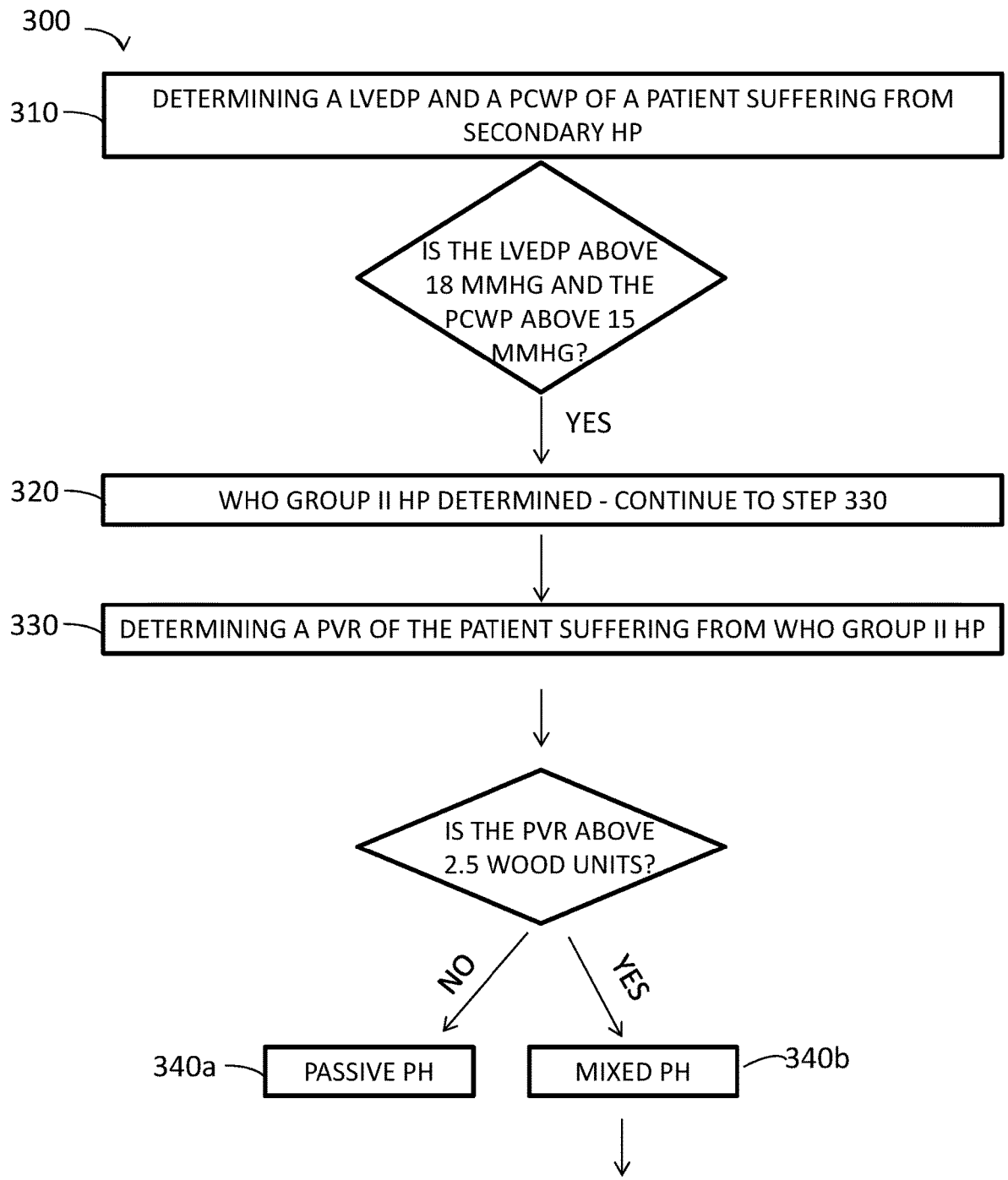
FIG. 3 is an illustrative flowchart of a method for ameliorating secondary pulmonary hypertension, according to some embodiments.

Reference is now made to FIG. 3 which is an illustrative flowchart of a method 300 for ameliorating WHO group II pulmonary hypertension, according to some embodiments. In step 310 a left ventricular end-diastolic pressure (LVEDP) and a pulmonary capillary wedge pressure (PCWP) of a patient suffering from secondary HP is determined. If the LVEDP is above 18 mmHg (or another suitable predetermined value, as described herein) and the PCWP above 15 mmHg (or another suitable predetermined value, as described herein), WHO group II PH is determined in step 320. In step 330 a pulmonary vascular resistance (PVR) of a patient suffering from secondary pulmonary hypertension is determined. If the PVR not above 2.5 Wood units (or another suitable predetermined value, as described herein), passive PH is determined, as in step 340a and no further action is taken. If the PVR above 2.5 Wood units, mixed PH is determined, as in step 340b, the method proceeds to step 350. In step 350 a change in the PVR in response to a reduction in PCWP (for example in response to a diuretic and/or a vasodilator) is determined. If the PVR has declined, the PH is determined to be reactive, as in step 360a and no further action is taken. If the PVR has not declined, the PH is determined to be fixed (i.e. non-reactive) as in step 360b, and the method proceeds to step 370. In step 370 the patient is treated with a pulmonary artery manipulation device to provide pulmonary artery denervation.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A method for determining a patient's suitability for a pulmonary artery denervation treatment, the method comprising:
    obtaining information regarding a pulmonary capillary wedge pressure (PCWP) and/or a left ventricular end-diastolic pressure (LVEDP); and
    treating the patient with a pulmonary artery manipulation device to provide pulmonary artery denervation only if the PCWP is above 15 mmHg or the LVEDP is above 18 mmHg, thereby ameliorating the pulmonary hypertension of the patient;
    wherein treating the patient with a pulmonary artery manipulation device comprises positioning the pulmonary artery manipulation device in a pulmonary artery, and impairing the activity of at least one sympathetic nerve, nerve fiber or neuron, thereby denervating the pulmonary artery; and
    wherein the patient suffers from pulmonary hypertension.

2. The method of claim 1, wherein obtaining information regarding the PCWP comprises determining the PCWP of the patient.

3. The method of claim 1, wherein obtaining information regarding the LVEDP comprises determining the LVEDP of the patient.

4. The method of claim 1, wherein the patient suffers from secondary pulmonary hypertension comprises WHO group II pulmonary hypertension, WHO group III pulmonary hypertension, WHO group IV pulmonary hypertension or WHO group V pulmonary hypertension.

5. The method of claim 4, wherein the WHO group II pulmonary hypertension comprises left heart disease associated pulmonary hypertension, wherein WHO group III pulmonary hypertension comprises chronic obstructive pulmonary disease pulmonary hypertension and/or interstitial lung disease associated pulmonary hypertension, wherein WHO group IV pulmonary hypertension comprises chronic thromboembolic associated pulmonary hypertension, and wherein WHO group V pulmonary hypertension comprises connective tissue disease associated pulmonary hypertension.

6. The method of claim 1, further comprising obtaining information regarding a selection treatment provided to the patient.

7. The method of claim 6, wherein the selection treatment comprises treating the patient with diuretics, vasodilators, chronic heart failure treatments, oxygen, antihypertensives or any combination thereof.

8. The method of claim 6, wherein the selection treatment comprises: calcium channel blockers, ACE inhibitors, beta blockers, digoxin, theophylline, PDE5 inhibitors, prostacyclins, endothelin receptor antagonists, nitric oxide, adenosine or any combination thereof.

9. The method of claim 8, wherein the selection treatment further comprises exercise, intravascular volume challenge, right heart catheterization, volume challenge during right heart catherization, cardiac echo, CT, MM, pulmonary angiogram, ECG, spirometry, lung volume assessment, lung ventilation/perfusion (VQ) scan, blood tests, or any combination thereof.

10. The method of claim 1, wherein the pulmonary artery manipulation device is configured to emit an unfocused ultrasound beam.

11. The method of claim 10, wherein the ultrasound beam is emitted at a frequency of 10-40 Mhz.

* * * * *